United States Patent [19]

Lisec

[11] Patent Number: 5,134,279
[45] Date of Patent: Jul. 28, 1992

[54] PHOTO-OPTICAL BULK STREAM DETECTOR FOR A CONDUIT

[76] Inventor: Peter Lisec, Bahnhofstrasse 34, A-3363 Amstetten-Hausmening, Austria

[21] Appl. No.: 618,376

[22] Filed: Nov. 27, 1990

[30] Foreign Application Priority Data

Nov. 27, 1989 [AU] Australia .............. 2708/89

[51] Int. Cl.$^5$ .............................. G06M 7/00
[52] U.S. Cl. ...................... 250/223 R; 222/64
[58] Field of Search ............ 250/222.1, 223 R, 561; 222/64

[56] References Cited

U.S. PATENT DOCUMENTS

| 4,319,568 | 3/1982 | Tregoning ............ 222/64 |
| 4,349,734 | 9/1982 | DiGuiseppi . |
| 4,699,273 | 10/1987 | Suggi-Liverani et al. ..... 250/223 R |
| 5,003,188 | 3/1991 | Igari ............... 250/223 R |

FOREIGN PATENT DOCUMENTS

| 517732 | 9/1979 | Australia . |
| 0195176 | 9/1988 | European Pat. Off. . |
| 1586284 | 5/1970 | Fed. Rep. of Germany . |
| 2310659 | 9/1974 | Fed. Rep. of Germany . |
| 3224862 | 10/1983 | Fed. Rep. of Germany . |
| 3431322 | 9/1985 | Fed. Rep. of Germany . |
| 3710694 | 10/1988 | Fed. Rep. of Germany . |
| 254731 | 3/1988 | German Democratic Rep. . |
| 380634 | 9/1964 | Switzerland . |
| 1130691 | 10/1968 | United Kingdom . |

*Primary Examiner*—David C. Nelms
*Assistant Examiner*—Que T. Le
*Attorney, Agent, or Firm*—Young & Thompson

[57] ABSTRACT

A bulk stream detector for a conduit (4, 5) feeding granular, hygroscopic material to be filled into spacer frames (3) for insulating glass from a storage container to a filling head (1) comprises a punctiform light source (8, 9) connected to the conduit (4, 5), this light source emitting a light beam (11) traversing the conduit. A sensor (10) responding to the light (11) emitted by the light source (8, 9) is arranged in opposition to the light source (8, 9). The sensor (10), under the effect of the light impinging thereon from the light source (8, 9), transmits a signal to a control unit (12, 13) which latter, in turn, transmits a signal if, during a preselected period of time after the last signal transmitted by the sensor (10), no signal has been received from the sensor (10).

5 Claims, 1 Drawing Sheet

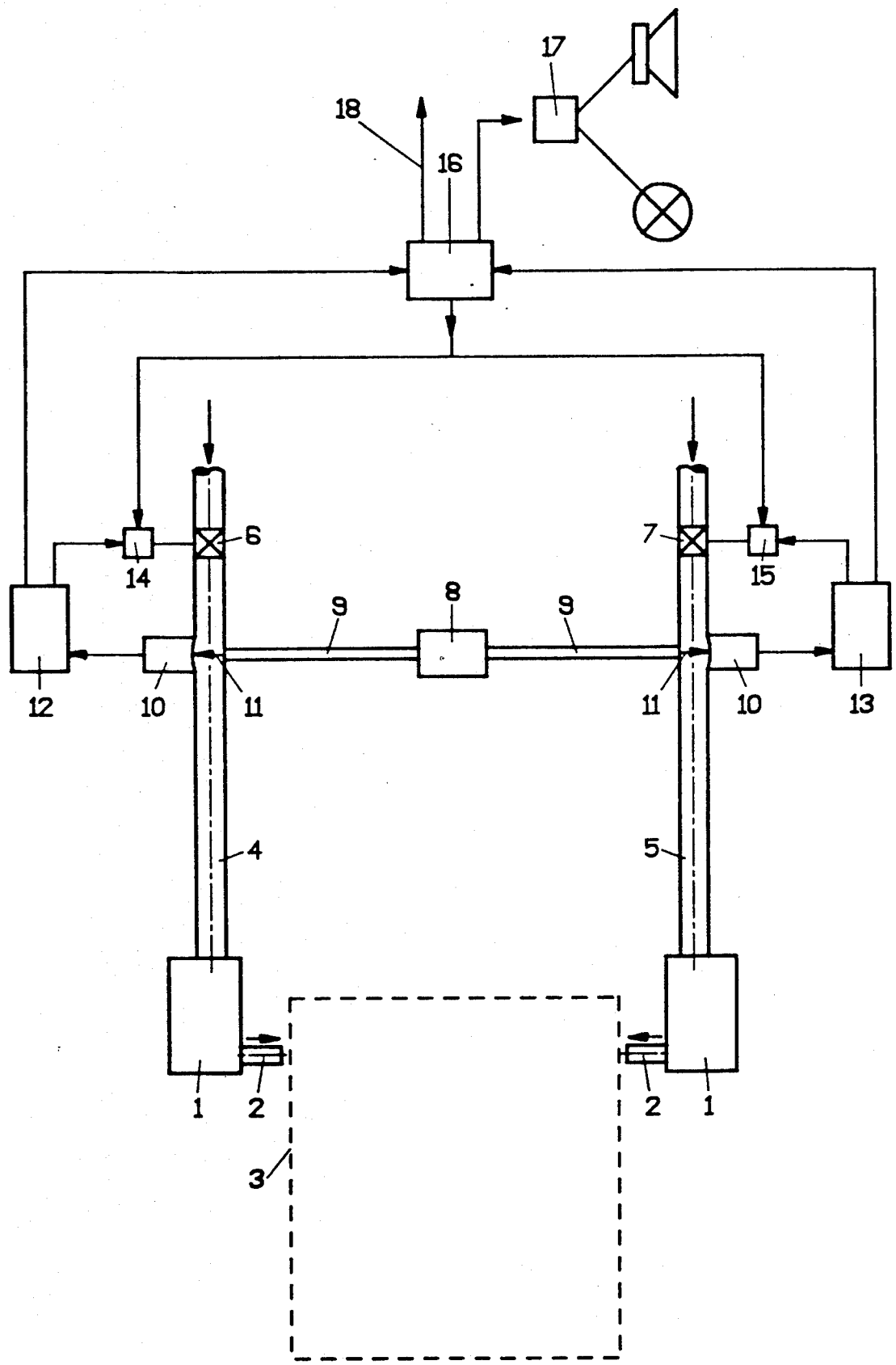

PHOTO-OPTICAL BULK STREAM DETECTOR FOR A CONDUIT

The invention relates to a bulk stream detector for a conduit wherein granulated material is conveyed, especially for a conduit supplying granular, hygroscopic material to be introduced into spacer frames for insulating glass from a storage container to a filling head.

EP-B-195,176 discloses an apparatus for filling hollow bodies with granulated material wherein the movements of granulated material in the conduit through which the granulated material is transported are monitored in accordance with the radar principle. The device according to EP-B-195,176 is controlled by means of signals transmitted by the bulk stream detector. The filling of spacer frames for insulating glass panes with hygroscopic material in granular form is cited as the preferred practical application of the device known from EP-B-b 195,176.

The invention is based on the object of indicating a bulk stream detector of the type discussed above which is of a simpler structure and consequently less expensive and yet permits reliable monitoring of granular streams moving within conduits.

According to the invention, this object has been attained by providing that a preferably punctiform light source, transmitting a light beam traversing the conduit, is arranged at the conduit, and that a sensor responding to the light emitted by the light source is located in opposition to the light source.

The invention is based on the realization that granulated material flowing through a conduit will temporarily interrupt the light beam continuously emitted by the light source so that the light beam, thus impinging intermittently on the sensor lying in opposition to the light source, can be utilized for detection of the bulk stream.

In a practical embodiment, the provision is made to provide, as the essentially punctiform light source, a fiber-optic cable comprising optionally bundled optical fibers or, respectively, that the sensor is a photodiode or the like.

A preferred embodiment of the detector according to this invention is distinguished in that the sensor, under the effect of the light impinging thereon from the light source, transmits a signal; that a control unit is connected with the sensor, receiving the signals transmitted by the sensor; and that the control unit transmits a signal if, during a preselected period of time after the last signal transmitted by the sensor, no signal is received from the sensor. In this embodiment, the circumstance is exploited that the light beam emitted by the light source is blocked for some time and/or remains absolutely interrupted in case the granulated material in the conduit is at a standstill; this occurs, for example, once a spacer frame has been completely filled with hygroscopic material or in case the flow of granules through the conduit is interrupted on account of some disturbance of the apparatus (clogging).

The last-described embodiment makes it possible, according to a further development of the invention, to operatively connect the control unit with a shutoff element associated with the conduit, and to close off the shutoff element upon reception of a signal from the control unit.

In a modification of the detector according to the invention, the provision is made that the control unit or the sensor transmits a signal if the number of signals fed thereto and/or the number of the light pulses received thereby per unit time drops below a preselected value. This embodiment serves for the production of a signal when the conduit transporting the granulated material is empty, so that a constant light beam impinges on the detector. The signal then transmitted by the sensor can be utilized for triggering an optical and/or acoustic signal or, alternatively, for interrupting the filling process performed on spacer frames.

For devices for filling spacer frames with two conduits each leading to a filling head through which simultaneously a spacer frame for insulating glass panes is being filled, as known from EP-B-195,176, the detector according to this invention can be distinguished in that the two control units connected to the sensors are coupled with each other by way of a comparator member transmitting at least one signal if one of the coupled-together control units, triggered by the sensor associated therewith, transmits a signal by a given time span earlier than the control unit associated with the other conduit. This embodiment is based on the fact that ordinarily the filling step executed by the two filling heads on the respectively associated halves of the spacer frames is, in the normal case, terminated at substantially the same point in time. If one of the sensors transmits its signal earlier by a preselected time span (normally 1-2 seconds) than the other sensor, then a disturbance can be concluded, or it can be concluded that the feeding of granulated material to one of the conduits is disturbed.

In the last-mentioned embodiment, it is preferred that the comparator member is connected to the control units of the drive mechanisms for the shutoff elements associated with the conduits, and that both shutoff elements are sealed by the drive mechanisms by a signal transmitted by the comparator member.

Ordinarily, the detector of this invention is characterized in that the light beam emanating from the light source traverses the conduit in a plane perpendicular to the axis of the conduit.

Additional details and features as well as advantages of the detector according to this invention can be seen from the following description wherein reference is had to the appended drawing which shows schematically a device, equipped with detectors according to this invention, for filling hollow members material).

BRIEF DESCRIPTION OF DRAWING

The sole FIGURE is a schematic representation of an embodiment of the invention.

The device can be constructed as known from EP-B-195,176 or DOS 3,224,862.

The device illustrated schematically in the drawing comprises two filling heads 1 feeding, by way of extensions 2 projecting therefrom, the hygroscopic, granular material supplied from a storage container, not shown in detail, or from storage containers, into the interior of a spacer frame 3 consisting of hollow moldings or of a hollow molding bent into a frame, by way of conduits 4 and 5.

Shutoff elements 6 and 7 are provided in conduits 4 and 5 for controlling the filling step.

Respectively one fiber-optic cable 9 terminates in an opening in the wall of conduits 4 and 5 and transmits a light beam emanating from a light source 8 and traversing the conduits 4 and 5 in a Plane substantially perpendicular to the conduit axis, as indicated by arrows 11.

The light beams symbolized by arrows 11, emanating from the ends of the fiber-optic cables 9 connected to the conduits 4 and 5, impinge on sensors 10 arranged in diametrical opposition to the ends 9 and 10 of the fiber-optic cables 9. The sensors 10, designed, for example, as photodiodes or other light-sensitive devices, transmit a signal upon impingement of a light beam 11. The signal transmitted by the sensors 10 is passed on to a control unit 12 and 13, respectively, connected to the sensors 10.

The control units 12 and 13 are designed so that they transmit a signal to the control unit for the drive mechanisms 14 and 15, respectively, of the shutoff elements 6 and 7, respectively, the control units for the drive mechanisms 14 and 15 then closing the associated shutoff elements 6 and 7. The control units 12 and 13 transmit a signal to the control units for the drive mechanisms 14, 15 of the shutoff elements 6 and 7 if no signal has been received during a preselectable time period by the sensor 10 which occurs if the granulated material fills conduit 4 or 5 completely and is at a standstill therein so that the light emitted by the fiber-optic cables 9 can no longer impinge on the sensors 10.

The sensors 10 are furthermore designed so that they transmit a signal to the associated control unit 12 or 13 if the number of light pulses received by the sensors per unit time drops below a preselectable value. This case occurs if the movement of the granulated material in the conduits 4 and 5 slows down, admitting the conclusion that the filling step for the spacer frame 3 has been completed. Alternatively, the provision can also be made that the control units 12, 13 transmit corresponding signals if they receive, from the sensor 10 associated therewith, within the unit of time less signals corresponding to light pulses received by the sensor.

As shown in the drawing, the control units 12 and 13 are connected with each other via a comparator member 16 which receives signals from control units 12 and 13 in each case when these units also transmit signals to the control units for the drive mechanisms 14 and 15 of the shutoff elements 6 and 7. The comparator member 16 determines the time difference between reception of a signal from control unit 12 and a signal received from control unit 13 and transmits, in case the time difference exceeds a preselected time span, a signal to both control units of the drive mechanisms 14 and 15 of shutoff elements 6 and 7, whereupon the latter are closed. Additionally, the provision can be made that the comparator member 16 transmits a signal to an optical and/or acoustic signaling device 17 so that it can be recognized that the filling step in one frame leg, e.g. the filling step of the filling head 1 located on the left-hand side in the drawing, has already been terminated whereas the sensor associated with the conduit 5 for the filling head 1 located on the right-hand side in the drawing has not as yet transmitted any signal.

There is also the possibility of providing that the comparator member 16 transmits a signal which places the total system at a standstill, as indicated by the arrow 18 in the drawing.

What is claimed is:

1. Bulk stream detector for a conduit (4, 5) through which granular, hygroscopic material, to be filled into spacer frames (3) for insulating glass, is conveyed from a storage container to a filling head (1), wherein a light source (8, 9) is arranged adjacent the conduit (4, 5) transmitting a light beam (11) traversing the conduit and, in opposition to the light source (8, 9), a sensor (10) is located which responds to the light (11) emitted by the light beam source (8, 9), and wherein the sensor (10) under the effect of the light impinging thereon from the light source (9) transmits a signal to a control unit (12, 13) connected with the sensor, this control unit (12, 13) transmitting, in turn, signals in dependence on the signals received from the sensor (10), said light source comprising a fiber-optic cable (9) comprising a bundle of optical fibers, the control unit (12, 13) transmitting a signal if, during a preselected period of time after the last signal transmitted by the sensor (10), no signal has been received from the sensor (10); and the control unit (12, 13) or the sensor (10) transmitting a signal if the number of signals fed thereto and/or the number of light pulses received thereby per unit time falls below a preselected value.

2. Detector according to claim 1, wherein the control unit (12, 13) is operatively connected with a shutoff element (6, 7) associated with the conduit (4, 5); and the shutoff element (6, 7) is closed upon reception of a signal from the control unit (12, 13).

3. Detector according to claim 1, wherein there are two said conduits (4, 5) leading to respectively to said filling head (1), through which simultaneously a spacer frame (3) for insulating glass panes is being filled, and wherein the two control units (12, 13) connected to the sensors (10) are coupled together by way of a comparator member (16) which latter transmits at least one signal if one of the connected control units (12, 13), triggered by the associated sensor (10), transmits a signal a predetermined time span earlier than the control unit (12, 13) associated with the other conduit.

4. Detector according to claim 3, wherein the comparator member (16) is connected with the control units for the drive mechanisms (14, 15) of the shutoff elements (6, 7) associated with the conduits (4, 5); and wherein, by means of a signal transmitted by the comparator member (16), both shutoff elements (6, 7) are closed off by the drive mechanisms (14, 15).

5. Detector according to claim 1, wherein the light beam (11) emanating from the light source (8, 9) traverses the conduit (4, 5) in a direction perpendicular to the axis of the conduit (4, 5).

* * * * *